(12) United States Patent
Randolph

(10) Patent No.: US 10,052,459 B2
(45) Date of Patent: Aug. 21, 2018

(54) CATHETER ASSEMBLY AND METHOD

(75) Inventor: James R. Randolph, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1003 days.

(21) Appl. No.: 13/348,043

(22) Filed: Jan. 11, 2012

(65) Prior Publication Data

US 2012/0197236 A1 Aug. 2, 2012

Related U.S. Application Data

(60) Provisional application No. 61/437,162, filed on Jan. 28, 2011.

(51) Int. Cl.
*A61M 25/00* (2006.01)
*A61M 25/09* (2006.01)
*A61M 25/01* (2006.01)

(52) U.S. Cl.
CPC ........ *A61M 25/09* (2013.01); *A61M 25/0102* (2013.01); *A61M 25/09025* (2013.01); *A61M 2025/0081* (2013.01); *A61M 2025/09083* (2013.01); *A61M 2025/09175* (2013.01)

(58) Field of Classification Search
CPC .................. A61M 25/09; A61M 25/00; A61M 2025/09091; A61M 2025/09175; A61M 2025/0081; A61M 25/0102; A61M 25/01; A61M 2025/09083; A61M 2025/09061; A61M 2025/09058; A61M 25/0105; A61M 2025/09075

USPC ... 604/95.01, 523–532, 170.01, 170.02, 104, 604/164.13, 510
See application file for complete search history.

(56) References Cited

U.S. PATENT DOCUMENTS

| | | | |
|---|---|---|---|
| 4,498,482 A | | 2/1985 | Williams |
| 4,676,249 A | | 6/1987 | Arenas et al. |
| 4,798,598 A | * | 1/1989 | Bonello ............ A61M 25/0136 600/436 |
| 4,813,925 A | * | 3/1989 | Anderson, Jr. ..... A61M 27/008 604/517 |
| 4,884,579 A | * | 12/1989 | Engelson .............. A61M 25/09 600/434 |
| 4,917,102 A | | 4/1990 | Miller et al. |
| 5,040,543 A | * | 8/1991 | Badera ............ A61M 25/09025 600/434 |
| 5,203,772 A | | 4/1993 | Hammerslag et al. |
| 5,383,923 A | | 1/1995 | Webster, Jr. |
| 5,472,435 A | * | 12/1995 | Sutton ................... A61M 27/00 604/540 |
| 5,554,114 A | | 9/1996 | Wallace et al. |
| 5,573,520 A | | 11/1996 | Schwartz et al. |

(Continued)

*Primary Examiner* — Kevin C Sirmons
*Assistant Examiner* — Tiffany Legette-Thompson
(74) *Attorney, Agent, or Firm* — Liell & McNeil

(57) ABSTRACT

A catheter assembly includes a wire guide having a helical outer wire and a non-helical core wire slidable within the outer wire between an advanced position and a retracted position. The outer wire includes a steering tip having a medium stiffness and a bending bias, and the core wire includes a higher stiffness and a straightening bias. The assembly further includes a catheter slidable over the outer wire to a steering configuration. A distal catheter end includes a compliant lower stiffness, and is adjustable in the steering configuration between a straight shape and a curved shape.

20 Claims, 5 Drawing Sheets

(56) References Cited

U.S. PATENT DOCUMENTS

| | | | | |
|---|---|---|---|---|
| 5,709,874 A | * | 1/1998 | Hanson | A61F 2/06 |
| | | | | 424/423 |
| 5,776,079 A | * | 7/1998 | Cope | A61M 25/0152 |
| | | | | 600/585 |
| 6,254,550 B1 | | 7/2001 | McNamara et al. | |
| 6,270,496 B1 | | 8/2001 | Bowe et al. | |
| 6,527,732 B1 | * | 3/2003 | Strauss | A61M 25/09 |
| | | | | 600/585 |
| 7,058,456 B2 | | 6/2006 | Pierce | |
| 2007/0049899 A1 | * | 3/2007 | Chambers | A61M 25/0041 |
| | | | | 604/500 |
| 2008/0312578 A1 | * | 12/2008 | DeFonzo | A61M 25/003 |
| | | | | 604/6.16 |
| 2010/0022989 A1 | * | 1/2010 | Parasmo | A61M 25/001 |
| | | | | 604/528 |
| 2010/0082059 A1 | * | 4/2010 | Gellman | A61B 17/221 |
| | | | | 606/200 |
| 2010/0179509 A1 | * | 7/2010 | Pyles | A61M 25/0041 |
| | | | | 604/506 |

* cited by examiner

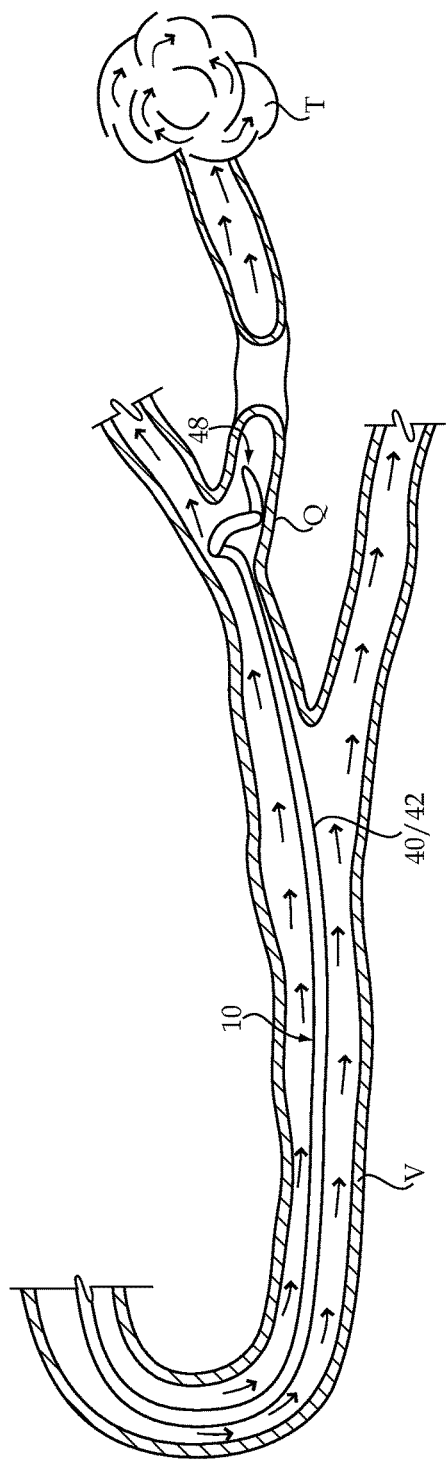
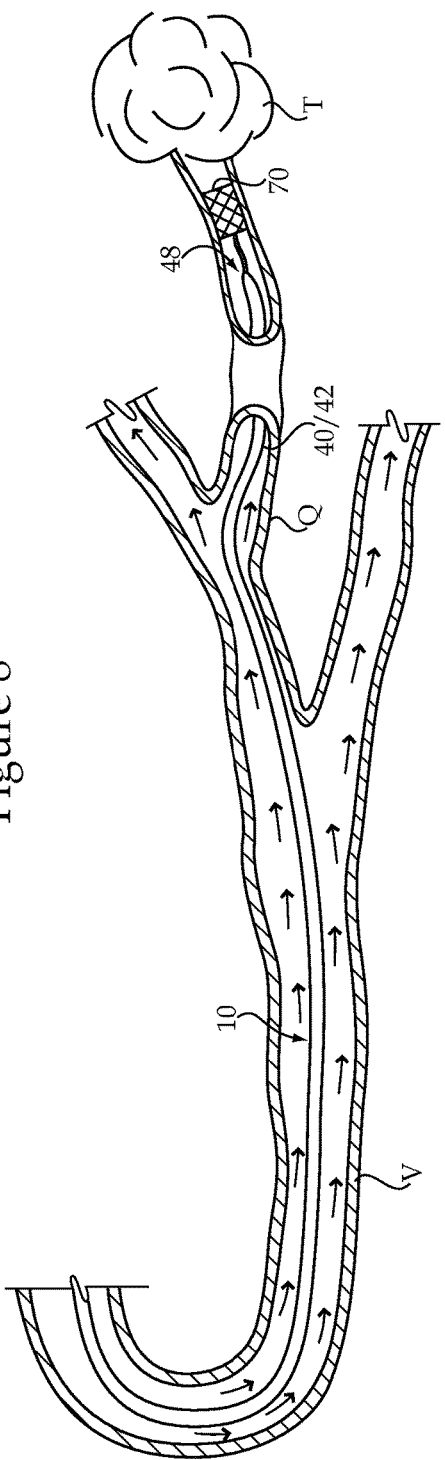
Figure 8
Figure 9 ial patent
CATHETER ASSEMBLY AND METHOD

RELATION TO OTHER PATENT APPLICATION

This application claims priority to provisional patent application 61/437,162, filed Jan. 28, 2011 with the same title.

TECHNICAL FIELD

The present disclosure relates generally to catheters used in performing intraluminal procedures, and relates more particularly to advancing a catheter through a body lumen in a patient in a curved shape defined at least in part by a bending bias of a helical outer wire of a wire guide.

BACKGROUND

A great many different types of minimally invasive treatment and diagnostic procedures are used in human patients. Techniques for percutaneous access to the cardiovascular system to enable the placement of stents and filters for embolization procedures, infusion of thrombolytic agents, and for still other purposes are well known. A typical percutaneous procedure involves accessing a body lumen to be treated by way of an opening formed in the patient's skin. Once access into a body lumen is achieved, a physician typically manipulates treatment or navigational devices from a location outside of the patient to advance through the body lumen until a target location for performing a procedure is reached. Accessing certain body lumens or portions thereof in this manner is relatively routine. Placing filters and other devices within certain relatively larger vascular lumens such as the inferior vena cava or the superior vena cava, for example, is considered relatively straightforward. Access to deeper portions of the cardiovascular system, and by way of smaller and more tortuous vascular lumens such as those perfusing internal organs or located deep within a limb and relatively far from the access opening, tends to be substantially more time consuming and difficult.

A variety of different guiding devices, commonly in the form of wire guides, are well known and widely used for many different intraluminal procedures. In one typical example, a wire guide is passed through the vascular lumen to a location of interest, often with the assistance of radiography, by way of various turns and branches within the body lumen. A flexible and often curved tip of the wire guide facilitates navigation to a location of interest. A catheter or other treatment mechanism can then be advanced over the wire guide, following its path through the body lumen, and navigating through turns, branches, or other features in a way facilitated by the already placed wire guide. Over decades of practical application of this general technique, technological advances in the design and use of wire guides, catheters and the like have enabled physicians to perform procedures within or near increasingly difficult to access portions of body lumens. Despite such technological advances, various portions of body lumens remain beyond reach, or considered impractical to attempt to navigate.

SUMMARY

In one aspect, a method of performing an intraluminal procedure on a patient includes sliding a catheter over a steering tip of a helical outer wire of a wire guide positioned within a body lumen of a patient, the steering tip having a bending bias. The method further includes relieving a straightening bias of a non-helical core wire of the wire guide on the steering tip. The method further includes applying the bending bias of the steering tip to the catheter in response to relieving the straightening bias, and advancing the catheter through the body lumen in a curved shape defined at least in part by the bending bias.

In another aspect, a catheter assembly includes a wire guide including a helical outer wire having a steering tip, and a non-helical core wire freely slidable within the outer wire between an advanced position within the steering tip, and a retracted position. The core wire has a higher stiffness and a straightening bias, and the steering tip has a medium stiffness and a bending bias. The catheter assembly further includes a catheter including an elongate catheter body having a longitudinal passage formed therein extending between a proximal catheter end and a distal catheter end. The elongate catheter body has an outer diameter dimension within the distal catheter end equal to less than about 2 millimeters and is freely slidable over the outer wire to position the catheter assembly in a steering configuration at which the distal catheter end is positioned over the steering tip. The distal catheter end includes a lower stiffness and is compliant with each of the curving bias and the straightening bias, and is further adjustable in the steering configuration between a straight shape defined at least in part by the straightening bias and a curved shape defined at least in part by the bending bias, via sliding the core wire between the advanced and retracted positions, respectively.

BRIEF DESCRIPTION OF THE DRAWINGS

FIG. 8 is a side diagrammatic view of a portion of the treatment system of FIG. 4 at yet another stage of the treatment procedure; and FIG. 9 is a side diagrammatic view of a portion of the system of FIG. 4 at yet another stage of the treatment procedure.

DETAILED DESCRIPTION

Figure 1:
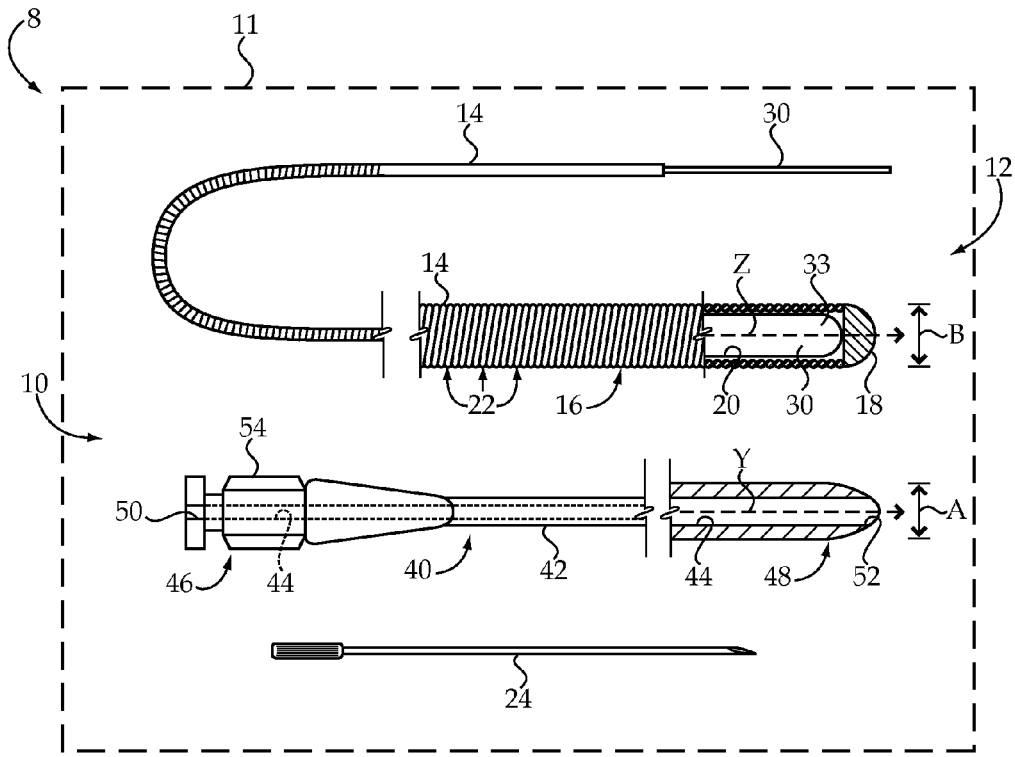
FIG. 1 is a partially sectioned side diagrammatic view of a packaged intraluminal treatment system, according to one embodiment.

Referring to FIG. 1, there is shown an intraluminal treatment system 8 according to one embodiment. System 8 may include a plurality of different components, positioned within a sterile package 11, and being configured for performing intraluminal treatment procedures on a patient, as further described herein. Sterile package 11 may include a sealed, peel-open pouch in one embodiment. System 8 may include a catheter assembly 10 including a wire guide 12 and a catheter 40, and a piercing needle 24 for gaining access such as by percutaneous entry to a body lumen within a patient. Additional components such as fittings, an introducer sheath and possibly still other components such as an additional wire guide may be included in sterile package 11. As will be further apparent from the following description, system 8 may be uniquely adapted for positioning catheter 40 within difficult to access and/or deep portions of a body lumen such as a vascular lumen within a patient.

Wire guide 12 may include a helical outer wire 14 having a steering tip 16, and a non-helical core wire 30 freely slidable within outer wire 14 between an advanced position within steering tip 16, and a retracted position. Core wire 30 may include a range of positions between a fully advanced position shown in FIG. 1 at which a distal tip 33 of core wire 30 contacts or is just adjacent to a terminal end piece 18 of outer wire 14, and a retracted position at which core wire 30 is fully retracted from steering tip 16, the significance of which will be apparent from the following description. In one embodiment, outer wire 14 may include a constant pitch spirally wound wire having a plurality of windings 22 defining a helix. Core wire 30 may be positioned coaxially with the helix, and may include a larger gauge linear wire, whereas outer wire 14 may include a smaller gauge wire. In one embodiment, wire guide 12 consists essentially of outer wire 14, core wire 30, and terminal end piece 18.

Catheter 40 may include an elongate catheter body 42 having a longitudinal passage 44 formed therein extending between a proximal catheter end 46 and a distal catheter end 48. A manifold 54 may be coupled with proximal catheter end 46 and has a fluid inlet 50 formed therein and connecting with longitudinal passage 44. Distal catheter end 48 may include a fluid outlet 52 formed therein and connecting with longitudinal passage 44. In certain embodiments, components of system 8 may be configured for accessing relatively small body lumens such as small veins or arteries. To this end, certain dimensions of the various components may be adapted to enable wire guide 12 and catheter 40 to be advanced through veins or arteries having an outer diameter dimension less than about 3 millimeters, and in some instances less than about 2.5 millimeters or even less than about 2.0 millimeters. Elongate catheter body 42 may define a longitudinal axis Y, and may include an outer diameter dimension normal to axis Y and within distal catheter end 48 which is equal to less than about 3 millimeters, and which may be equal to less than about 2 millimeters, and even less than about 1.0 millimeters in certain embodiments. A bore size of longitudinal passage 40 may be just slightly larger than an outer diameter dimension of a helix defined by helical outer wire 14, as discussed herein. In FIG. 1, the subject outer diameter dimension is shown via arrow A. As used herein, the term "about" should be understood in the context of a number of significant digits. Thus, about 3 millimeters means between 2.5 and 3.4 millimeters, about 2.5 millimeters means between 2.45 and 2.54 millimeters, and so on.

As mentioned above, core wire 30 may be positioned coaxially with a helix defined by outer wire 14. Core wire 30 may define a longitudinal axis Z, which in the configuration shown in FIG. 1 is overlapping with a longitudinal helix axis defined by outer wire 14 and thus commonly labeled therewith. The helix defined by outer wire 14 may include an outer diameter dimension shown via arrow B which is equal to less than about 0.5 millimeters in certain embodiments. In addition to dimensional attributes of certain components of system 8 which facilitate accessing and advancing through relatively small and/or tortuous body lumens, relative stiffnesses and shape properties of certain of the components may be configured such that a unique and advantageous steering and advancement technique is possible with system 8.

To this end, core wire 30 may have a higher stiffness and a straightening bias. This should be understood to mean that core wire 30 may be considered relatively stiff compared with other components of catheter assembly 10, and may include a shape memory property such that when core wire 30 is deflected or bent in directions transverse to axis Z, it will have a tendency to return to a relatively straight shape. Steering tip 16 of outer wire 14 may in contrast include a medium stiffness and a bending bias. This should be understood to mean that steering tip 16 is moderately stiff in comparison to other components of catheter assembly 10, and when no dominant biasing force is applied thereto, will have a tendency to assume a bent or curved shape. As will be further apparent from the following description, a variety of bent or curved shapes, including shapes bending or curving in three dimensions, may be associated with a rest or unbiased state of outer wire 14. The terms "bending" and "curving" are generally used interchangeably herein, however, in some instances a given shape having only sharp angles as opposed to smooth angles might be better characterized as merely bent rather than curved. In contrast, a curved shape may be understood as continuously bent and without sharp angles. Thus, the description of steering tip 16 as having a bending bias should be understood to mean that it has a tendency to assume at least a bent shape, which may also be a curved shape. In FIG. 1, wire guide 14 is shown as it might appear where the straightening bias of core wire 30 is applied to steering tip 16 such that steering tip 16 assumes a straight shape. As further described herein, when core wire 30 is slid within outer wire 14 to a refracted position, a portion of steering tip 16 which is not presently subjected to a straightening bias of core wire 30 may assume a curved shape in accordance with a shape memory property of outer wire 14 within steering tip 16. These properties of core wire 30 and outer wire 14 may be leveraged to control and vary a shape of catheter 40. In this vein, distal catheter end 48 of catheter 40 may include a lower stiffness, and is compliant with each of the bending bias and the straightening bias. As further described herein, catheter 40 may be freely slidable over outer wire 14 when outer wire 14 is positioned within lumen 44 to place catheter assembly 10 in a steering configuration at which distal catheter end 48 is positioned over steering tip 16. In the steering configuration, distal catheter end 48 is adjustable between a straight shape defined at least in part by the straightening bias and a curved shape defined at least in part by the bending bias, via sliding core wire 30 between the advanced position and one of many possible retracted positions, respectively.

Figure 2:
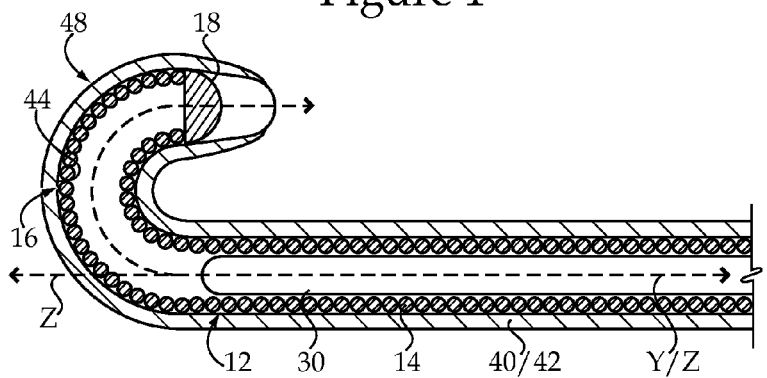
FIG. 2 is a partially sectioned side diagrammatic view of a portion of a catheter assembly, according to one embodiment.

Referring also now to FIG. 2, there is shown catheter assembly 10 as it might appear in the steering configuration with distal catheter end 48 positioned over steering tip 16, and core wire 30 retracted in a distal to proximal direction from terminal end piece 18 such that the bending bias of steering tip 16 is applied to distal catheter end 48, and distal catheter end 48 assumes a J-shape defined at least in part by the bending bias. Another way to understand the configuration depicted in FIG. 2 is that the straightening bias of core wire 30 has been relieved on steering tip 16, or a portion thereof, and steering tip 16 has assumed or begun to assume a curved shape consistent with its shape memory properties. As alluded to above, the shape assumed by steering tip 16 when the straightening bias of core wire 30 is relieved might be more sharply angular than that shown, and thus more fairly characterized as bent in certain embodiments. Moreover, since steering tip 16 may be bending or curving against a resistance to deformation of distal catheter end 48, the actual shapes assumed by steering tip 16 within distal catheter end 48 may differ from those assumed where a shape of steering tip 16 is manipulated outside of distal catheter end 48. Responsive to relieving the straightening bias on distal catheter end 48, distal catheter end 48 has assumed or begun to assume a curved shape such as the curved J-shape shown. It may further be noted from FIG. 2 that longitudinal axis Y of elongate catheter body 42 overlaps with longitudinal axis Z of core wire 30 for a portion of an axial length of catheter body 42, but curves away from longitudinal axis Z within the portion of catheter body 42 comprising distal catheter end 48 positioned over steering tip 16. As further described herein, a wide variety of curved shapes of distal catheter end 42 which are assumed responsive to curved shapes of steering tip 16 are possible.

Figure 3:
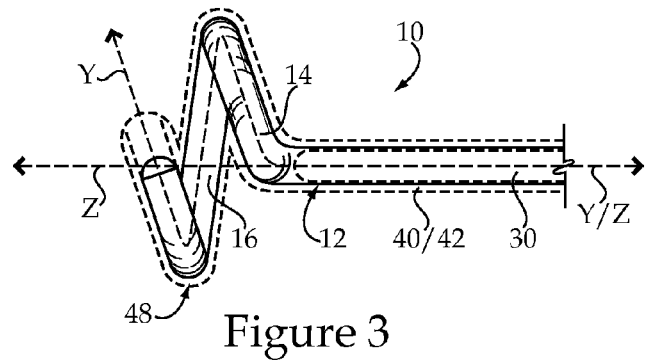
FIG. 3 is a side diagrammatic view of a portion of the catheter assembly of FIG. 2, shown in a different configuration.

Referring also to FIG. 3, there is shown one example additional curved shape which may be assumed by distal catheter end 48 in response to the bending bias of steering tip 16. In FIG. 3, core wire 30 has been further retracted relative to its position shown in FIG. 2, and a relatively greater proportion of steering tip 16 has been relieved of the straightening bias of core wire 30. It may be further noted from FIG. 3 that longitudinal axis Y of elongate catheter body 42 lies within a number of planes greater than one. In other words, in the curved J-shape of distal catheter end 48 shown in FIG. 2, longitudinal axis Y may lie within a single plane, the plane of the page, whereas in FIG. 3 longitudinal axis Y curves out of the plane of the page, and thus lies within more than one plane. Still other curved configurations for distal catheter end 48 are possible, such as a circular shape, an irregular shape, a helical shape which enlarges in a distal direction, or becomes smaller in a distal direction. Each of these shapes might be attained by designing steering tips to have different rest shapes assumed when no dominant straightening bias is applied. For instance, a clinician might have available a set of wire guides, or at least a set of helical outer wires, each of which is capable of assuming a different rest shape, and any one of which might be used in a catheter assembly as described herein, depending upon the shape or other characteristics of a body lumen to be navigated. Since each individual wire guide may also have a range of different shapes of its steering tip, it will further be understood that an essentially infinite number of different curved shapes of distal catheter end 48 may be possible via manipulating core wire 30 to different positions within outer wire 14.

INDUSTRIAL APPLICABILITY

Figure 4:
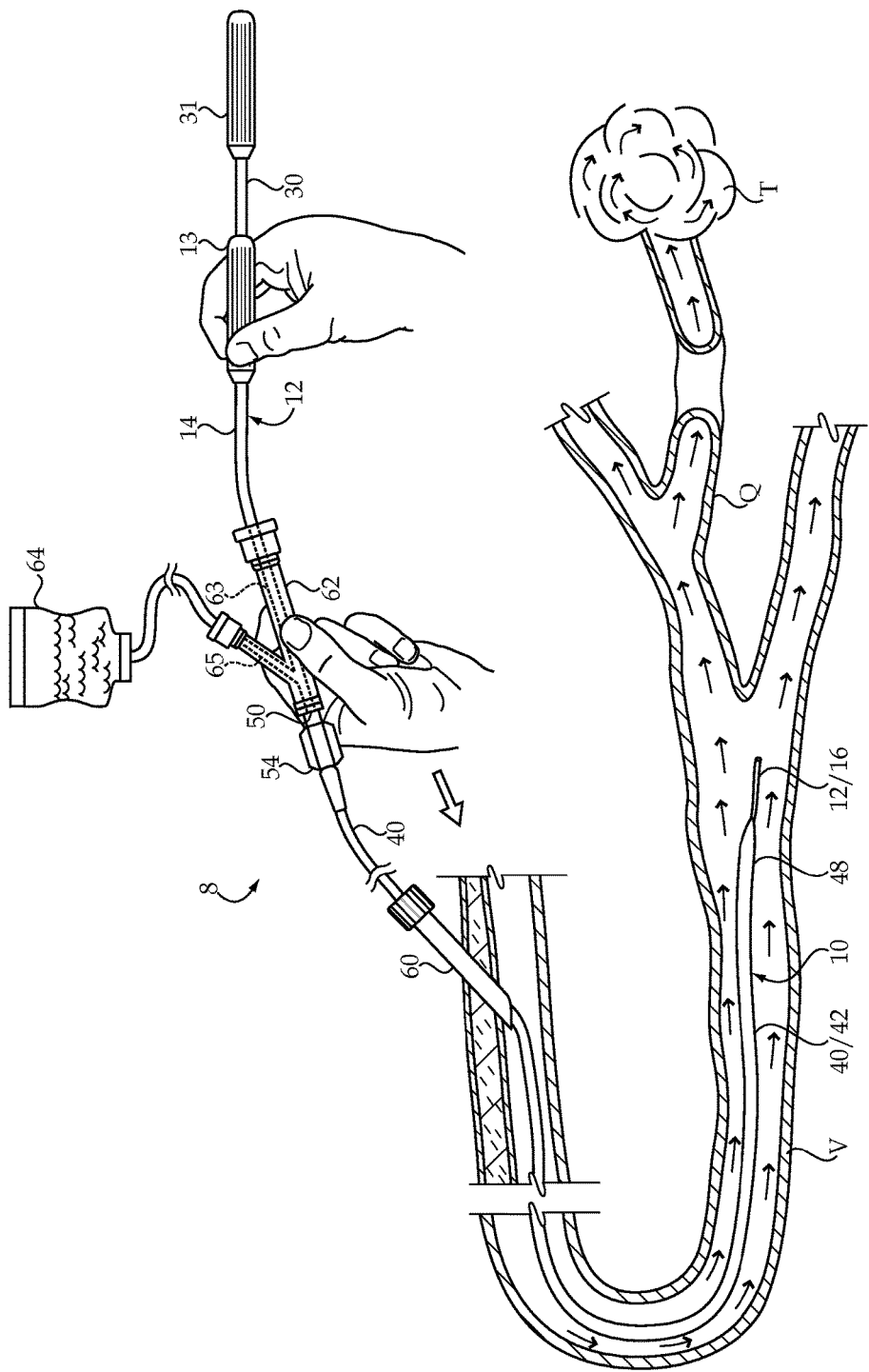
FIG. 4 is a side diagrammatic view of an intraluminal treatment system at one stage of an intraluminal treatment procedure, according to one embodiment.

Turning now to FIG. 4, there is shown system 8 as it might appear during one stage of an intraluminal treatment procedure on a patient. Wire guide 12 has been passed by way of an introducer sheath 60 into a body lumen V of a patient such as a vein or artery. Catheter 40 has been advanced over wire guide 12 in a conventional manner through body lumen V, such that a portion of wire guide 12 extends distally above catheter 40 as shown in FIG. 4. A Y-fitting 62 is coupled with manifold 54, and includes a first passage 65 fluidly connecting longitudinal passage 44 of catheter 40 with a fluid reservoir 64 positioned outside the patient. A second passage 63 in Y-fitting 62 receives wire guide 12 such that wire guide 12 extends through passage 63 and into longitudinal passage 44 of catheter 40. A first handle 13 is coupled with outer wire 14, and a second handle 31 is coupled with core wire 30 such that a clinician can manipulate the position of catheter 40 relative to wire guide 12, and also manipulate a position of core wire 30 within outer wire 14 as further described herein.

It should be appreciated that the illustration in FIG. 4 is exemplary only, and that a variety of other fitting types and the like, as well as introducer mechanisms might be used without departing from the present disclosure. Moreover, versions are contemplated in which a fluid reservoir is not connected with catheter 40, or is connected only after guiding catheter 40 to a target location within the body lumen, and wire guide 12 withdrawn. It may be desirable to utilize a fluid reservoir such as fluid reservoir 64 for conveying a contrast agent or the like into body lumen V to assist in imaging, or for other purposes.

In FIG. 4, a treatment site T such as a tumor or other undesired tissue is supplied with blood from lumen V by way of a branch lumen Q. To position catheter 40 at a target location upstream of treatment site T, it is necessary for catheter 40 to navigate through a plurality of turns within and/or between lumen V and branch lumen Q. As discussed above, manipulation of catheter 40 relative to wire guide 12, and manipulation of outer wire 14 and core wire 30 relative to one another, can provide advantageous techniques for navigating catheter 40 to its intended target location.

Figure 5:
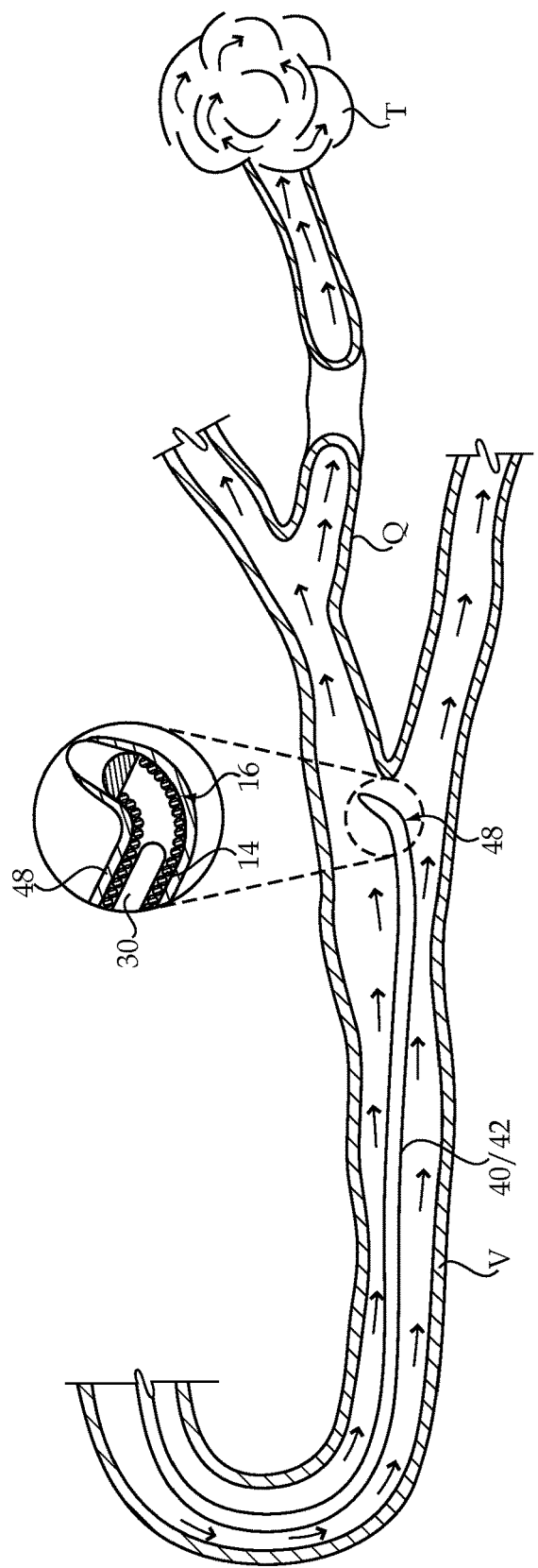
FIG. 5 is a side diagrammatic view, including a detailed enlargement, of a portion of the system of FIG. 4 at another stage of the treatment procedure.
Figure 6:
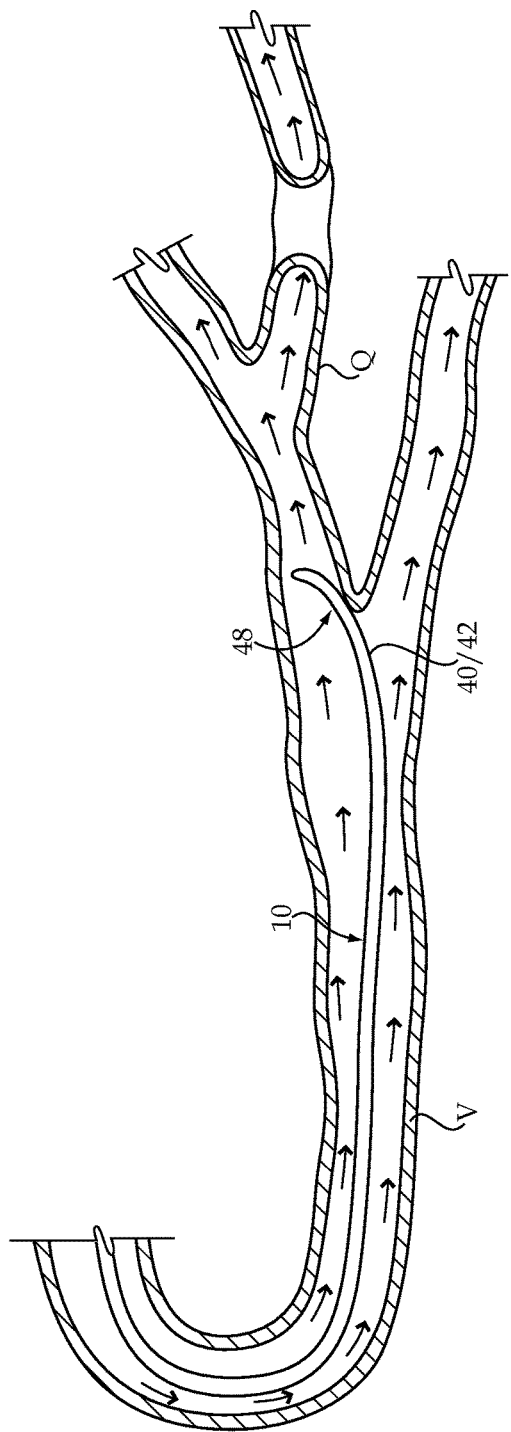
FIG. 6 is a side diagrammatic view of a portion of the system of FIG. 4 at another stage of the treatment procedure.

Referring also to FIG. 5, there is shown catheter assembly 10 as it might appear where catheter body 42 and in particular distal catheter end 48 has been slid over wire guide 12 to position distal catheter end 48 over steering tip 16 and place catheter assembly 10 in the steering configuration. As depicted in the detailed enlargement of FIG. 5, the straightening bias of core wire 30 on a portion of steering tip 16 has been relieved by sliding core wire 30 proximally such that a portion of outer wire 14 relieved of the straightening bias has assumed a curved shape. In response to relieving the straightening bias, a bending bias of steering tip 16 on distal catheter end 48 has been applied to render the curved shape of distal catheter end 48 shown in FIG. 5. From the stage shown in FIG. 5, catheter 40 may be advanced through a turn in body lumen V while maintaining distal catheter end 48 stationary over steering tip 16. Referring also to FIG. 6, there is shown catheter 40 as it might appear where distal catheter end 48 has been advanced in the curved shape through the turn in body lumen V and into an upper branch thereof.

Figure 7:
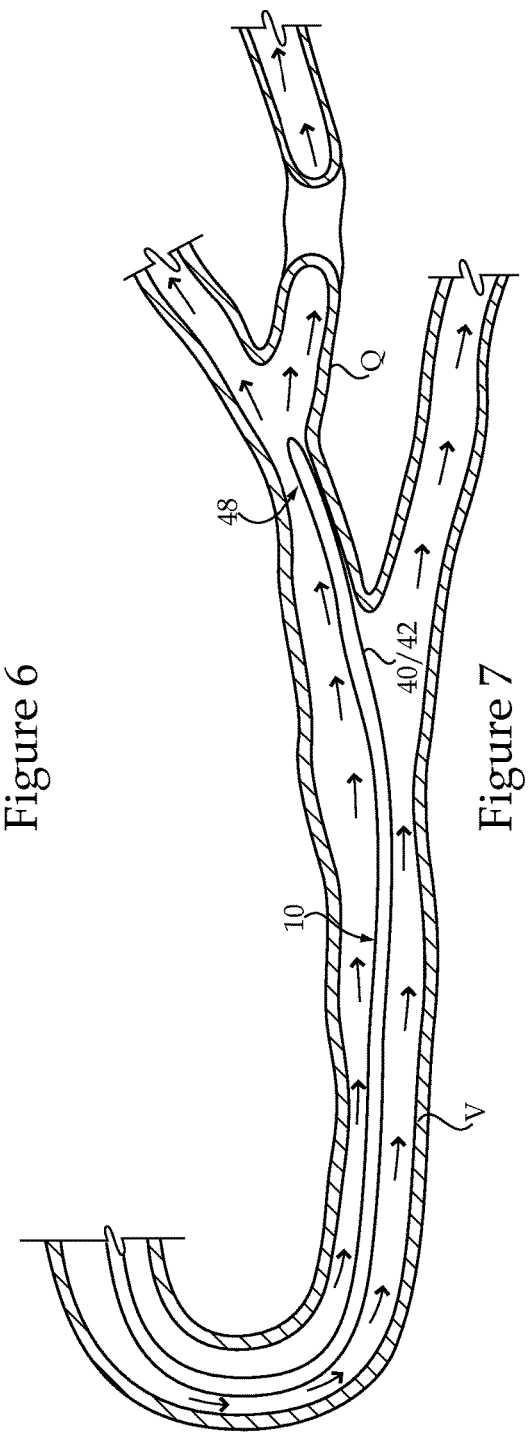
FIG. 7 is a side diagrammatic view of a portion of the treatment system of FIG. 4 at yet another stage of the treatment procedure.

Referring also to FIG. 7, after negotiating the turn within body lumen V, the straightening bias of core wire 30 on steering tip 16 may be reapplied. This may include sliding core wire 30 in a distal direction such that it returns to the advanced position within outer wire 14, approximately as shown in FIG. 1. Reapplying the straightening bias may have the effect of relieving the bending bias on distal catheter end 48 such that it returns to a straight shape defined at least in part by the straightening bias. After or during reapplying the straightening bias, catheter assembly 10 may be further advanced through body lumen V to reach a state approximately as shown in FIG. 7. To reach a target location upstream of treatment site T, it may be necessary to navigate catheter 40 through another turn in body lumen V, such as upon entering branch lumen Q. Due to the size, sharpness, or geometry of the turn into branch lumen Q, it may be advantageous to advance catheter 40 through this turn in a curved shape different from the curved shape used in advancing through the turn as depicted in FIGS. 5 and 6. For instance, while a relatively modest curvature of distal catheter end 48 sufficed to readily navigate into the upper branch of lumen V at the first turn, a relatively more dramatically curved shape, and even a three dimensionally curved shape may be useful in readily accessing branch lumen Q. In one embodiment, the curved shape used in entering branch lumen Q may be a shape which is attained by retracting core wire 30 relatively further within outer wire 14 than what is done to attain the shape used in advancing through the first turn. A helical shape similar to that shown in FIG. 3 might be used, or a curved shape which results from positioning core wire 30 relative to outer wire 14 part way between the fully advanced position shown in FIG. 1 and the retracted position depicted in FIG. 3.

Referring also to FIG. 8, there is shown catheter assembly 10 where distal catheter end 48 is being advanced into branch lumen Q. In one embodiment, advancing distal catheter end 48 into branch lumen Q and adjusting distal catheter end 42 to the curved shape may take place simultaneously, such as by maintaining core wire 30 stationary while sliding catheter 40 and outer wire 14 together in a distal direction from a distal tip 33 of core wire 30. In other words, core wire 30 may be adjusted to a retracted position, relieving its straightening bias on steering tip 16 and thus distal catheter end 48, by maintaining core wire 30 stationary within a body lumen, but pushing catheter 40 and outer wire 14 through the body lumen relative to core wire 30. In response to relieving the straightening bias of core wire 30 on steering tip 16, it will tend to assume a curved shape, and distal catheter end 48 will likewise begin to assume a curved shape defined at least in part by the bending bias of steering tip 16. In FIG. 8, distal catheter end 48 may include a 3-dimensional curved shape such that distal catheter end 48 curves out of and into the page in FIG. 8, and then curves back into the page as it extends deeper into branch lumen Q.

Referring to FIG. 9, there is shown catheter assembly 10 as it might appear positioned at a target location upstream from treatment site T. At the target location, distal catheter end 48 may reside within a portion of branch lumen Q having an outer diameter dimension, i.e. a cross sectional thickness, less than about 2.5 millimeters, or even less than about 2.0 millimeters. Wire guide 12 has been withdrawn from catheter 40 to establish a body lumen access path such as through passage 44. A treatment mechanism 70 has been slid by way of the body lumen access path into a portion of branch lumen Q which is upstream from treatment site T, distal to the target location, and having an outer diameter dimension equal to less than about 2.0 millimeters. Treatment mechanism 70 has also been adjusted from a low profile or lumen access configuration which it will typically have while being slid through catheter 40 to an expanded or deployed configuration. In the embodiment shown, treatment mechanism 70 includes an embolization mechanism configured to form an embolus within branch lumen Q such that blood flow to treatment site T is blocked. From the state depicted in FIG. 9, catheter assembly 10 may be removed from the patient, and other appropriate post-procedural steps undertaken.

The concepts set forth in the present disclosure are expected to be applicable to accessing and performing treatment procedures within relatively small and/or difficult to access portions of body lumens. The desirability of treating tumors, vascular abnormalities, and still other problems deep within the cardiovascular system has long been recognized. Technology, however, has not kept pace with medical needs. On the one hand, it tends to be relatively difficult and expensive to manufacture catheters, wire guides, and other tools or treatment mechanisms which are small enough to even access relatively small body lumens. On the other hand, even where devices such as catheters and the like have been made quite small, they tend to suffer from shortcomings such as poor pushability and kinking. As a result, in the past clinicians have often chosen either to not treat particular problems, or have done so in modified ways which do not take full advantage of theoretical possibilities.

For instance, while clots, tumors, and other conditions residing deep within the cardiovascular system could theoretically be treated such as by way of embolization, angioplasty, or infusion of liquid treatment agents, medical professionals often decide to "over" treat a region which includes the abnormality of interest rather than performing a more focused procedure. The reasons for this may include the perception that attempting to navigate tight turns, or advance through constrictions or very narrow body lumens, will not be possible or will risk kinking, buckling, or other problems. In the case of the example embolization technique described herein, using conventional techniques embolization might be performed upstream of branch lumen Q rather than within branch lumen Q itself. As a result, blood flow would be blocked perhaps successfully. But instead of targeting blood flow blockage specifically to treatment site T, other portions of the vasculature perfused by body lumen V would also be blocked. Similarly, in the case of an infusion procedure, while it might have been recognized as ideal to infuse treatment agent directly into branch lumen Q, in the past a procedure would likely have been performed such that infusate was delivered upstream of branch lumen Q, and thus possibly supplying the treatment agent to locations other than those specifically targeted. Among other things, the present disclosure offers reduced risk of kinking or buckling a catheter and greater access to small body lumens, since wire guide 14 can provide structural support which enhances pushability in a relatively small catheter size.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of performing an intraluminal procedure on a patient with a catheter assembly that includes a wire guide with a helical outer wire having a steering tip, and a non-helical core wire freely slidable within the helical outer wire between an advanced position within the steering tip, and a retracted position, the core wire having a higher stiffness and a straightening bias, and the steering tip having a medium stiffness and a bending bias; and a catheter including an elongate catheter body that extends from a distal tip of a distal catheter end to a proximal catheter end, and having a longitudinal passage formed therein extending between the proximal catheter end and the distal catheter end, and the longitudinal passage opens through the distal catheter end along a longitudinal axis, and the elongate catheter body having a rest shape that is straight and an outer diameter dimension within the distal catheter end equal to less than about 2 millimeters, and being freely slidable over the helical outer wire to position the catheter assembly in a steering configuration at which the distal catheter end is positioned over the steering tip, and a bore size of the longitudinal passage being larger than an outer diameter of the helical outer wire at the distal catheter end when the steering tip is positioned proximal to the distal catheter end;

and the distal catheter end having a lower stiffness and being compliant with each of the curving bias and the straightening bias, and further being adjustable in the steering configuration between a straight shape defined at least in part by the straightening bias and a curved shape defined at least in part by the bending bias, via sliding the core wire between the advanced and retracted positions, respectively, and a wall of the elongate catheter body at the distal catheter end having a uniform thickness proximal segment contiguous with a thinning thickness distal segment, and wherein the catheter assembly has a guiding configuration in which the steering tip of the wire guide is positioned outside the catheter and extends distally beyond the distal catheter end, and the method comprising the steps of: sliding the catheter over the steering tip of the helical outer wire of the wire guide positioned within a body lumen of a patient, the steering tip having the bending bias; relieving the straightening bias of the non-helical core wire of the wire guide on the steering tip; applying the bending bias of the steering tip to the catheter in response to relieving the straightening bias; and advancing the catheter through the body lumen in a curved shaped defined at least in part by the bending bias.

2. The method of claim 1 wherein the step of advancing further includes advancing the catheter through a turn in the body lumen, and further comprising a step of maintaining a distal end of the catheter stationary over the steering tip during advancing through the turn.

3. The method of claim 2 further comprising a step of reapplying the straightening bias to the steering tip after the step of advancing.

4. The method of claim 3 further comprising a step of advancing the catheter through another turn in the body lumen in a different curved shape defined at least in part by the bending bias.

5. The method of claim 4 further comprising a step of reapplying the bending bias during the step of advancing the catheter through another turn.

6. The method of claim 5 wherein the step of reapplying the bending bias includes maintaining the non-helical core wire stationary while sliding the catheter and helical outer wire in a distal direction from a distal tip of the non-helical core wire.

7. The method of claim 4 wherein the step of advancing the catheter through another turn includes advancing the catheter in a three-dimensional curved shape.

8. The method of claim 3 wherein each of the relieving and reapplying steps includes sliding the non-helical core wire relative to the helical outer wire.

9. The method of claim 8 further comprising a step of establishing a lumen access path through the catheter via withdrawing the helical outer wire and the non-helical core wire from the catheter.

10. The method of claim 9 further comprising positioning the distal end of the catheter by way of the advancing step at a target location within a vein or artery comprising the body lumen and having an outer diameter less than about 2.5 millimeters.

11. The method of claim 10 further comprising a step of sliding a treatment mechanism by way of the lumen access path into a portion of the vein or artery distal to the target location and having an outer diameter less than about 2.0 millimeters.

12. The method of claim 11 further comprising the steps of adjusting the treatment mechanism from a lumen access configuration to a deployed configuration within the vein or artery, and forming an embolus via the treatment mechanism within the vein or artery.

13. A catheter assembly comprising:
a wire guide including a helical outer wire having a steering tip, and a non-helical core wire freely slidable within the helical outer wire between an advanced position within the steering tip, and a retracted position, the core wire having a first stiffness and a straightening bias, and the steering tip having a second stiffness, which is less stiff than the first stiffness, and a bending bias; and
a catheter including an elongate catheter body that extends from a distal tip of a distal catheter end to a proximal catheter end, and having a longitudinal passage formed therein extending between the proximal catheter end and the distal catheter end, and the longitudinal passage opens through the distal catheter end along a longitudinal axis, and the elongate catheter body having a rest shape that is straight and an outer diameter dimension within the distal catheter end equal to less than about 2 millimeters, and being freely slidable over the helical outer wire to position the catheter assembly in a steering configuration at which the distal catheter end is positioned over the steering tip, and a bore size of the longitudinal passage being larger than an outer diameter of the helical outer wire at the distal catheter end when the steering tip is positioned proximal to the distal catheter end;
the distal catheter end having a third stiffness, which is less stiff than the second stiffness, and being compliant with each of the curving bias and the straightening bias, and further being adjustable in the steering configuration between a straight shape defined at least in part by the straightening bias and a curved shape defined at least in part by the bending bias, via sliding the core wire between the advanced and retracted positions, respectively, and a wall of the elongate catheter body at the distal catheter end having a uniform thickness proximal segment contiguous with a thinning thickness distal segment; and
wherein the catheter assembly has a guiding configuration in which the steering tip of the wire guide is positioned outside the catheter and extends distally beyond the distal catheter end.

14. The catheter assembly of claim 13 wherein the outer diameter dimension of the elongate catheter body is equal to less than about 2 millimeters, and wherein the helical outer wire defines a helix having an outer diameter dimension equal to less than about 0.5 millimeters.

15. The catheter assembly of claim 14 wherein the outer diameter dimension of the elongate catheter body is equal to less than about 1.0 millimeters.

16. The catheter assembly of claim 14 wherein the helical outer wire includes a constant pitch spirally wound wire having a first gauge, and the core wire includes a linear wire having a second gauge, which is a larger gauge than the first gauge.

17. The catheter assembly of claim 14 wherein the core wire is positioned coaxially with the helix.

18. The catheter assembly of claim 17 wherein the wire guide further includes a terminal end piece attached to the helical outer wire, and the wire guide consists essentially of the terminal end piece, the helical outer wire, and the core wire.

19. The catheter assembly of claim 17 wherein the curved shape includes a J-shape.

20. The catheter assembly of claim 17 wherein the elongate catheter body defines a longitudinal axis, and in the curved shape the longitudinal axis lies within a number of planes greater than one.

\* \* \* \* \*